US012053145B2

(12) United States Patent
Endo

(10) Patent No.: US 12,053,145 B2
(45) Date of Patent: Aug. 6, 2024

(54) MEDICAL IMAGE PROCESSING APPARATUS AND METHOD

(71) Applicant: FUJIFILM Corporation, Tokyo (JP)

(72) Inventor: Maiko Endo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 372 days.

(21) Appl. No.: 17/382,293

(22) Filed: Jul. 21, 2021

(65) Prior Publication Data
US 2021/0350534 A1 Nov. 11, 2021

Related U.S. Application Data

(63) Continuation of application No. PCT/JP2020/004024, filed on Feb. 4, 2020.

(30) Foreign Application Priority Data

Feb. 19, 2019 (JP) .................. 2019-027513

(51) Int. Cl.
A61B 1/00 (2006.01)
G06T 7/00 (2017.01)

(52) U.S. Cl.
CPC .... A61B 1/000094 (2022.02); A61B 1/00004 (2013.01); A61B 1/000096 (2022.02); (Continued)

(58) Field of Classification Search
CPC .......... A61B 1/00004; A61B 1/000094; A61B 1/000096; A61B 1/00043; (Continued)

(56) References Cited

U.S. PATENT DOCUMENTS

2003/0095692 A1* 5/2003 Mundy ................ G06T 7/0012 382/128
2005/0207630 A1* 9/2005 Chan .................... G06T 7/0012 382/131

(Continued)

FOREIGN PATENT DOCUMENTS

JP 2014-188223 A 10/2014
JP 2016-158681 A 9/2016

(Continued)

OTHER PUBLICATIONS

Maayan Frid-Adar,"GAN-based synthetic medical image augmentation for increased CNN performance in liver lesion classification," Sep. 21, 2018, Neurocomputing 321 (2018),pp. 321-328.*

(Continued)

Primary Examiner — Omar S Ismail
(74) Attorney, Agent, or Firm — Studebaker & Brackett PC

(57) ABSTRACT

A medical image processing apparatus includes an image acquisition unit that acquires a medical image, a classifier that classifies the medical image or a region of interest included in the medical image into any of two or more classes based on a feature amount obtained from the medical image, a reliability calculation unit that calculates reliability of a classification result of the medical image or the region of interest from the classifier, and a confirmation unit that confirms the classification result of the medical image or the region of interest based on the calculated reliability.

24 Claims, 6 Drawing Sheets

(52) U.S. Cl.
CPC ........ *A61B 1/00043* (2013.01); *G06T 7/0012* (2013.01); *G06T 2207/10068* (2013.01); *G06T 2207/20081* (2013.01); *G06T 2207/20084* (2013.01); *G06T 2207/20104* (2013.01); *G06T 2207/30096* (2013.01)

(58) Field of Classification Search
CPC . G06T 2207/10068; G06T 2207/20081; G06T 2207/20084; G06T 2207/20104; G06T 2207/30096; G06T 7/0012; G06V 10/82; G06V 2201/03
See application file for complete search history.

(56) References Cited

U.S. PATENT DOCUMENTS

| | | | | |
|---|---|---|---|---|
| 2008/0130970 | A1* | 6/2008 | Niemeyer | G06T 7/0012 382/128 |
| 2010/0189326 | A1* | 7/2010 | McGinnis | G06T 7/0012 382/131 |
| 2014/0286561 | A1* | 9/2014 | Remiszewski | G06V 30/1916 382/133 |
| 2015/0347464 | A1* | 12/2015 | Takata | G16H 50/00 707/728 |
| 2015/0356271 | A1* | 12/2015 | Kozuka | A61B 6/563 705/2 |
| 2016/0014328 | A1 | 1/2016 | Rokutanda | |
| 2016/0110584 | A1* | 4/2016 | Remiszewski | G06V 20/69 382/133 |
| 2016/0125162 | A1* | 5/2016 | Takata | G16H 30/40 705/2 |
| 2016/0232425 | A1* | 8/2016 | Huang | G06F 18/253 |
| 2017/0091413 | A1* | 3/2017 | Kondo | G16H 50/20 |
| 2017/0098301 | A1 | 4/2017 | Ikemoto et al. | |
| 2018/0075597 | A1* | 3/2018 | Zhou | A61B 6/032 |
| 2018/0225820 | A1* | 8/2018 | Liang | G06V 10/82 |
| 2018/0300878 | A1* | 10/2018 | Ihara | G06T 7/0012 |
| 2018/0315188 | A1* | 11/2018 | Tegzes | G06T 7/11 |
| 2019/0080454 | A1* | 3/2019 | Hameed | G06T 7/0014 |
| 2019/0205606 | A1* | 7/2019 | Zhou | G06F 18/285 |
| 2019/0267130 | A1* | 8/2019 | Takata | G16H 50/70 |
| 2020/0279368 | A1* | 9/2020 | Tada | A61B 1/00016 |
| 2020/0394792 | A1* | 12/2020 | Duval | G06T 5/40 |
| 2020/0405148 | A1* | 12/2020 | Tran | A61B 3/0016 |

FOREIGN PATENT DOCUMENTS

| | | |
|---|---|---|
| JP | 2017-213058 A | 12/2017 |
| JP | 2018-126632 A | 8/2018 |
| WO | 2018/225448 A1 | 12/2018 |

OTHER PUBLICATIONS

Kiichi Fukumaa,"A study on nuclei segmentation, feature extraction and disease stage classification for human brain histopathological images," Procedia Computer Science 96 ( 2016 ),pp. 1202-1209.*
Ruwan Nawarathna,"Abnormal image detection in endoscopy videos using a filter bank and local binary patterns," Jun. 11, 2014,Neurocomputing 144(2014), pp. 70-80.*
Jo Schlemper,"Attention gated networks: Learning to leverage salient regions in medical images," Feb. 5, 2019, Medical Image Analysis 53 (2019),pp. 197-205.*
Marc Aubreville,"Automatic Classification of Cancerous Tissue in Laserendomicroscopy Images of the Oral Cavity using Deep Learning," Sep. 20, 2017,Scientific Reports | 7: 11979 |, pp. 1-8.*
International Search Report issued in PCT/JP2020/004024; mailed Mar. 24, 2020.
International Preliminary Report on Patentability and Written Opinion issued in PCT/JP2020/004024; issued Aug. 10, 2021.
An Office Action; "Notice of Reasons for Refusal," mailed by the Japanese Patent Office on Feb. 3, 2023, which corresponds to Japanese Patent Application No. 2021-501819 and is related to U.S. Appl. No. 17/382,293; with English language translation.

* cited by examiner

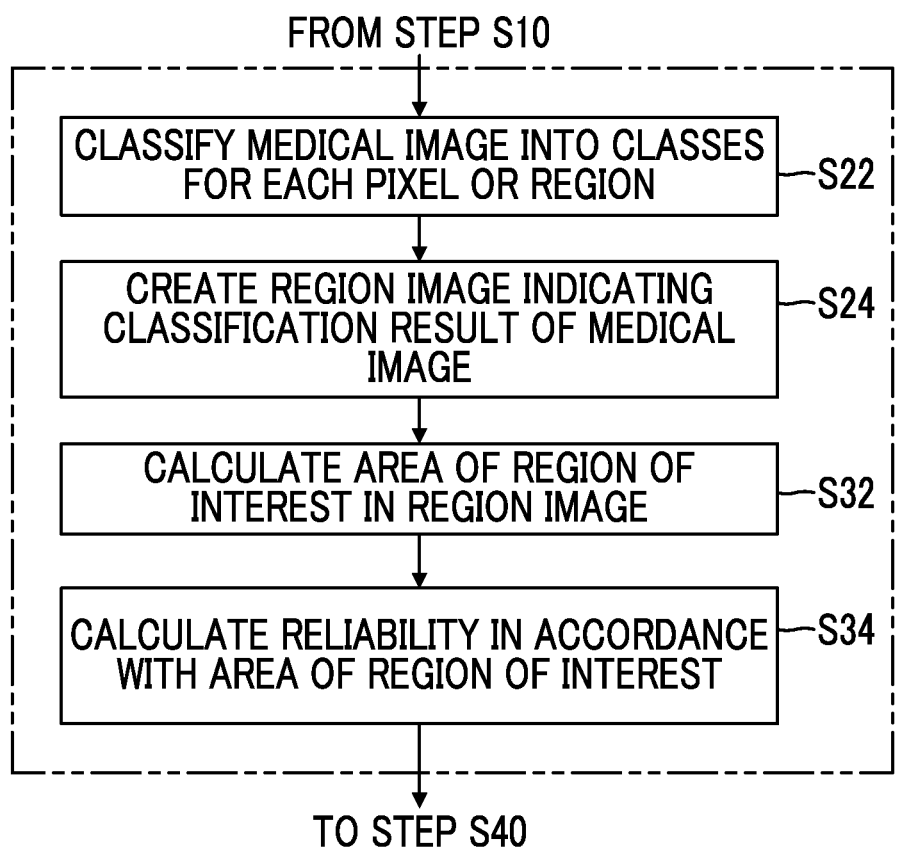

MEDICAL IMAGE PROCESSING APPARATUS AND METHOD

CROSS-REFERENCE TO RELATED APPLICATIONS

This application is a Continuation of PCT International Application No. PCT/JP2020/004024 filed on Feb. 4, 2020, which claims priority under 35 U.S.C § 119(a) to Japanese Patent Application No. 2019-027513 filed on Feb. 19, 2019. Each of the above application(s) is hereby expressly incorporated by reference, in its entirety, into the present application.

BACKGROUND OF THE INVENTION

1. Field of the Invention

The present invention relates to a medical image processing apparatus and a method, and particularly to a technology for automatically classifying a lesion or the like based on a medical image.

2. Description of the Related Art

In the related art, an image processing apparatus that supports observation or diagnosis of a user by classifying abnormality (lesion) or the like in a medical image for each pixel or region and displaying a region classified as the abnormality (lesion) included in the medical image in a highlighted manner has been suggested (JP2014-188223A and JP2018-126632A).

An image processing apparatus disclosed in JP2014-188223A classifies a medical image for each pixel or region and performs a focusing determination of "focused" or "non-focused" on the medical image for each pixel or region. The image processing apparatus corrects a classification result of each pixel or region of the medical image in accordance with a result of the focusing determination in the pixel or the region of the medical image. In a case where the result of the focusing determination of each pixel or region of the medical image is "non-focused", the classification result (classification result of a normal portion or a non-normal portion) of each pixel or region of the medical image corresponding to "non-focused" is corrected to indicate uncertainty.

Accordingly, reliability of highlighted display of an abnormal portion of the medical image is improved.

An image processing apparatus disclosed in JP2018-126632A calculates a score indicating presence or absence of a lesion and severity of the lesion for each pixel of a color medical image and evaluates reliability of the score calculated based on the color medical image. In a case of displaying a lesion portion of the medical image in a highlighted manner, the lesion portion is displayed in a highlighted manner based on the severity (score) of the lesion and the reliability of the score.

Here, the reliability of the score is evaluated depending on whether or not an imaging condition for the entire medical image is good based on a color balance of the color medical image.

The image processing apparatus disclosed in JP2018-126632A calculates the score indicating the severity of the lesion portion using color information on the lesion portion of the color medical image. Thus, in a case where the color information is not correct (for example, in a case where halation occurs, or in a case where any color channel (color component) is saturated), the reliability of the score is decreased.

A type of lesion to be determined by the image processing apparatus disclosed in JP2018-126632A can be selected in accordance with an examination content, and a lesion to be examined is selected in advance. In an example of the invention disclosed in JP2018-126632A, inflammation that is a lesion of inflammatory bowel disease is used as the lesion of a determination target, and the severity of the lesion is scored using the color information on the lesion portion.

SUMMARY OF THE INVENTION

In a case of automatically classifying benignancy, malignancy, or the like of the medical image or a region of interest included in the medical image based on the medical image, a problem arises in that the classification result is not stable due to a motion of a living body, a change in imaging position, and the like.

In the image processing apparatus disclosed in JP2014-188223A, in a case of displaying the abnormal portion included in the medical image in a highlighted manner, in order to improve the reliability of the highlighted display, an uncertain region is not included in the highlighted display of at least the abnormal portion by regarding the classification result of the pixel or the region of the medical image corresponding to "non-focused" as "uncertainty" using the result of the focusing determination for each pixel or region of the medical image. However, reliability of the classification result of the medical image or the region of interest included in the medical image is not improved. In addition, "uncertainty" is not the classification result of each pixel or region of the medical image.

Meanwhile, the lesion determined by the image processing apparatus disclosed in JP2018-126632A is decided, and the invention disclosed in JP2018-126632A does not improve reliability of the classification result of the lesion.

The present invention is conceived in view of such a matter, and an object thereof is to provide a medical image processing apparatus and a method capable of improving reliability of a classification result of a medical image or a region of interest included in the medical image.

In order to achieve the object, a medical image processing apparatus according to an aspect of the present invention comprises an image acquisition unit that acquires a medical image, a classifier that classifies the medical image or a region of interest included in the medical image into any of two or more classes based on a feature amount obtained from the medical image, a reliability calculation unit that calculates reliability of a classification result of the medical image or the region of interest from the classifier, and a confirmation unit that confirms the classification result of the medical image or the region of interest based on the reliability.

According to an aspect of the present invention, the classifier classifies the medical image or the region of interest included in the medical image into any of the two or more classes based on the feature amount obtained from the medical image. The classification result is not always stable. Therefore, the reliability calculation unit calculates the reliability of the classification result. While the confirmation unit confirms the classification result based on the calculated reliability, the confirmation unit does not confirm the classification result in a case where the calculated reliability does not satisfy a set condition. Accordingly, the reliability of the classification result confirmed by the confirmation unit can be improved.

In the medical image processing apparatus according to another aspect of the present invention, it is preferable that in a case where the reliability is greater than or equal to a threshold value, the confirmation unit confirms the classification result of the medical image or the region of interest.

In the medical image processing apparatus according to still another aspect of the present invention, it is preferable that the image acquisition unit acquires a time series of medical images, and the confirmation unit confirms the classification result of the medical image or the region of interest based on reliability of a plurality of classification results sequentially calculated for the time series of medical images by the reliability calculation unit.

In the medical image processing apparatus according to still another aspect of the present invention, it is preferable that in a case where the number of specific classification results for which the reliability calculated by the reliability calculation unit is greater than or equal to a threshold value is greater than or equal to a reference number, or in a case where a ratio of the number of specific classification results is greater than or equal to a reference ratio, the confirmation unit confirms the specific classification result as the classification result of the medical image or the region of interest.

In the medical image processing apparatus according to still another aspect of the present invention, it is preferable that the reliability calculation unit calculates an amount of change in reliability of a specific classification result among the plurality of classification results, and in a case where the amount of change in reliability of the specific classification result is within a reference range, the confirmation unit confirms the specific classification result as the classification result of the medical image or the region of interest.

In the medical image processing apparatus according to still another aspect of the present invention, it is preferable that the classifier classifies the medical image into the classes for each pixel or region based on the medical image and creates a region image indicating the classification result of the medical image, and the reliability calculation unit calculates the reliability of the classification result of the medical image or the region of interest based on the region image. In a case of creating the region image indicating the classification result of the medical image, the reliability of the classification result can be calculated using the created region image.

In the medical image processing apparatus according to still another aspect of the present invention, it is preferable that the reliability calculation unit calculates an area of the region of interest based on the region image, and in a case where the area of the region of interest is greater than or equal to a threshold value, the confirmation unit confirms the classification result of the medical image or the region of interest.

In the medical image processing apparatus according to still another aspect of the present invention, it is preferable that the reliability calculation unit calculates a representative value of the reliability of the classification result for each pixel in the region of interest based on the region image, and in a case where the calculated representative value of the reliability is greater than or equal to a threshold value, the confirmation unit confirms the classification result of the medical image or the region of interest.

In the medical image processing apparatus according to still another aspect of the present invention, it is preferable that the reliability calculation unit calculates a variance or a standard deviation of the classification result for each pixel in the region of interest based on the region image, and in a case where the calculated variance or standard deviation is less than or equal to a threshold value, the confirmation unit confirms the classification result of the medical image or the region of interest.

It is preferable that the medical image processing apparatus according to still another aspect of the present invention further comprises a threshold value setting unit that sets the threshold value to any value by an operation of a user.

It is preferable that the medical image processing apparatus according to still another aspect of the present invention further comprises a display control unit that displays the medical image acquired by the image acquisition unit and the classification result confirmed by the confirmation unit on a display unit. Accordingly, the user can determine that the classification result displayed on the display unit is confirmed.

In the medical image processing apparatus according to still another aspect of the present invention, it is preferable that after the classification result is displayed on the display unit, the display control unit causes the classification result to be not displayed after a certain time period. In a case where the classification result includes a plurality of pieces of information, the classification result may be caused to be not displayed by causing all of the plurality of pieces of information to be not displayed or causing a part of the plurality of pieces of information to be not displayed.

In the medical image processing apparatus according to still another aspect of the present invention, it is preferable that the display control unit displays the classification result of the medical image or the region of interest from the classifier and the classification result confirmed by the confirmation unit on the display unit in an identifiable manner. Accordingly, the user can check the non-confirmed classification result and the confirmed classification result.

A medical image processing method according to still another aspect of the present invention comprises a step of acquiring a medical image, a step of classifying the medical image or a region of interest included in the medical image into any of two or more classes based on a feature amount obtained from the medical image, a step of calculating reliability of a classification result of the medical image or the region of interest, and a step of confirming the classification result of the medical image or the region of interest based on the reliability.

According to the present invention, in a case of classifying the medical image or the region of interest included in the medical image into any of the two or more classes, the reliability of the classification result can be improved.

BRIEF DESCRIPTION OF THE DRAWINGS

FIG. 7 is a flowchart illustrating an embodiment of processing in steps S20 and S30 of the flowchart illustrated in FIG. 6.

DESCRIPTION OF THE PREFERRED EMBODIMENTS

Hereinafter, a preferable embodiment of a medical image processing apparatus and a method according to an embodiment of the present invention will be described in accordance with appended drawings.

[Overall Configuration of Endoscope System Including Medical Image Processing Apparatus]

Figure 1:
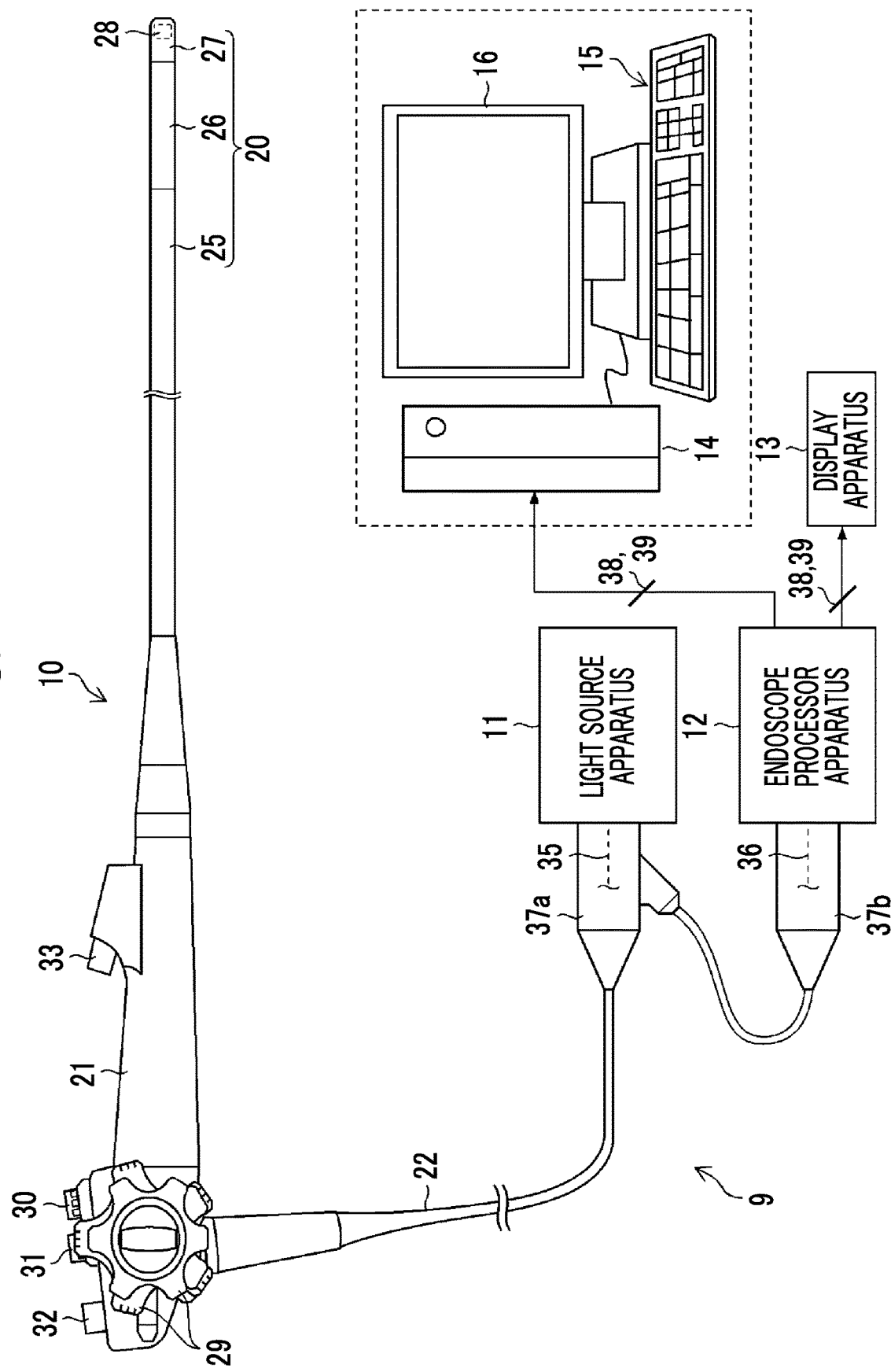
FIG. 1 is a schematic diagram illustrating an overall configuration of an endoscope system 9 including a medical image processing apparatus according to an embodiment of the present invention.

FIG. 1 is a schematic diagram illustrating an overall configuration of an endoscope system 9 including the medical image processing apparatus according to the embodiment of the present invention.

As illustrated in FIG. 1, the endoscope system 9 comprises an endoscope 10 that is an electronic endoscope, a light source apparatus 11, an endoscope processor apparatus 12, a display apparatus 13, a medical image processing apparatus 14, an operation unit 15, and a display 16.

The endoscope 10 images a time series of medical images including a subject image and is, for example, a flexible endoscope. The endoscope 10 includes an insertion part 20 that is inserted into a test object and has a distal end and a proximal end, a hand operation unit 21 that is consecutively installed on a proximal end side of the insertion part 20 and is held by an operator for performing various operations, and a universal cord 22 that is consecutively installed with the hand operation unit 21.

The entire insertion part 20 is formed in a long shape having a small diameter. The insertion part 20 is configured by consecutively installing, in order from the proximal end side toward a distal end side, a flexible portion 25 that has flexibility, a bending portion 26 that can be bent by operating the hand operation unit 21, and a distal end portion 27 that incorporates an imaging optical system (objective lens), not illustrated, an imaging element 28, and the like.

The imaging element 28 is an imaging element of a complementary metal oxide semiconductor (CMOS) type or a charge coupled device (CCD) type. Image light of an observed part is incident on an imaging surface of the imaging element 28 through an observation window, not illustrated, that is open on a distal end surface of the distal end portion 27, and an objective lens, not illustrated, that is arranged behind the observation window. The imaging element 28 outputs an imaging signal by imaging (converting into an electric signal) the image light of the observed part incident on the imaging surface.

Various operation members operated by the operator are disposed in the hand operation unit 21. Specifically, two types of bending operation knobs 29 that are used for a bending operation of the bending portion 26, an air supply and water supply button 30 for an air supply and water supply operation, and a suction button 31 for a suction operation are disposed in the hand operation unit 21. In addition, a still picture imaging instruction unit 32 for providing an imaging instruction for a still picture 39 of the observed part and a treatment tool introduction port 33 through which a treatment tool (not illustrated) is inserted into a treatment tool insertion path (not illustrated) passing through the insertion part 20 are disposed in the hand operation unit 21.

The universal cord 22 is a connection cord for connecting the endoscope 10 to the light source apparatus 11. The universal cord 22 includes a light guide 35 that passes through the insertion part 20, a signal cable 36, and a fluid tube (not illustrated). In addition, a connector 37a that is connected to the light source apparatus 11, and a connector 37b that branches from the connector 37a and is connected to the endoscope processor apparatus 12 are disposed in an end portion of the universal cord 22.

The light guide 35 and the fluid tube (not illustrated) are inserted into the light source apparatus 11 by connecting the connector 37a to the light source apparatus 11. Accordingly, necessary illumination light, water, and air are supplied to the endoscope 10 from the light source apparatus 11 through the light guide 35 and the fluid tube (not illustrated). Consequently, the observed part is irradiated with the illumination light from an illumination window (not illustrated) on the distal end surface of the distal end portion 27. In addition, in accordance with a push operation performed on the air supply and water supply button 30, air or water is ejected toward the observation window (not illustrated) on the distal end surface from an air supply and water supply nozzle (not illustrated) on the distal end surface of the distal end portion 27.

The signal cable 36 and the endoscope processor apparatus 12 are electrically connected by connecting the connector 37b to the endoscope processor apparatus 12. Accordingly, through the signal cable 36, the imaging signal of the observed part is output to the endoscope processor apparatus 12 from the imaging element 28 of the endoscope 10, and a control signal is output to the endoscope 10 from the endoscope processor apparatus 12.

The light source apparatus 11 supplies the illumination light to the light guide 35 of the endoscope 10 through the connector 37a. Light of various wavelength ranges corresponding to an observation purpose such as white light (light of a white wavelength range or light of a plurality of wavelength ranges), light of a specific one or plurality of wavelength ranges, or a combination thereof is selected as the illumination light. The specific wavelength range is a range narrower than the white wavelength range.

For example, a first example of the specific wavelength range is a blue range or a green range of a visible range. The wavelength range of the first example includes a wavelength range of greater than or equal to 390 nm and less than or equal to 450 nm or greater than or equal to 530 nm and less than or equal to 550 nm. Light of the first example has a peak wavelength in the wavelength range of greater than or equal to 390 nm and less than or equal to 450 nm or greater than or equal to 530 nm and less than or equal to 550 nm.

For example, a second example of the specific wavelength range is a red range of the visible range. The wavelength range of the second example includes a wavelength range of greater than or equal to 585 nm and less than or equal to 615 nm or greater than or equal to 610 nm and less than or equal to 730 nm. Light of the second example has a peak wavelength in the wavelength range of greater than or equal to 585 nm and less than or equal to 615 nm or greater than or equal to 610 nm and less than or equal to 730 nm.

A third example of the specific wavelength range includes a wavelength range of which a light absorption coefficient varies between oxyhemoglobin and reduced hemoglobin. Light of the third example has a peak wavelength in the wavelength range of which the light absorption coefficient varies between the oxyhemoglobin and the reduced hemoglobin. The wavelength range of the third example includes a wavelength range of 400±10 nm, 440±10 nm, 470±10 nm, or greater than or equal to 600 nm and less than or equal to 750 nm. Light of the third example has a peak wavelength in the wavelength range of 400±10 nm, 440±10 nm, 470±10 nm, or greater than or equal to 600 nm and less than or equal to 750 nm.

A fourth example of the specific wavelength range is a wavelength range (390 nm to 470 nm) of excitation light that is used for observing (fluorescence observation) fluorescence emitted by a fluorescent substance in a living body and excites the fluorescent substance.

A fifth example of the specific wavelength range is a wavelength range of infrared light. The wavelength range of the fifth example includes a wavelength range of greater than or equal to 790 nm and less than or equal to 820 nm or greater than or equal to 905 nm and less than or equal to 970 nm. Light of the fifth example has a peak wavelength in the wavelength range of greater than or equal to 790 nm and less than or equal to 820 nm or greater than or equal to 905 nm and less than or equal to 970 nm.

The endoscope processor apparatus 12 controls an operation of the endoscope 10 through the connector 37b and the signal cable 36. In addition, the endoscope processor apparatus 12 generates an image (referred to as a "motion picture 38") consisting of a time series of frame images 38a including the subject image based on the imaging signal acquired from the imaging element 28 of the endoscope 10 through the connector 37b and the signal cable 36. Furthermore, in a case where the still picture imaging instruction unit 32 is operated in the hand operation unit 21 of the endoscope 10, the endoscope processor apparatus 12 sets one frame image of the motion picture 38 as the still picture 39 corresponding to a timing of the imaging instruction in parallel with generation of the motion picture 38.

The motion picture 38 and the still picture 39 are medical images obtained by imaging an inside of the test object, that is, an inside of the living body. Furthermore, in a case where the motion picture 38 and the still picture 39 are images obtained by the light (special light) of the specific wavelength range, both images are special light images. The endoscope processor apparatus 12 outputs the generated motion picture 38 and the still picture 39 to each of the display apparatus 13 and the medical image processing apparatus 14.

The endoscope processor apparatus 12 may generate (acquire) the special light image having information on the specific wavelength range based on a normal light image obtained by the white light. In this case, the endoscope processor apparatus 12 functions as a special light image acquisition unit. The endoscope processor apparatus 12 obtains a signal of the specific wavelength range by performing calculation based on color information on red, green, and blue (RGB) or cyan, magenta, and yellow (CMY) included in the normal light image.

In addition, for example, the endoscope processor apparatus 12 may generate a feature amount image such as a well-known oxygen saturation image based on at least one of the normal light image obtained by the white light or the special light image obtained by the light (special light) of the specific wavelength range. In this case, the endoscope processor apparatus 12 functions as a feature amount image generation unit. Any of the motion picture 38 or the still picture 39 including the image of the inside of the living body, the normal light image, the special light image, and the feature amount image is a medical image obtained by imaging a result of imaging or measuring a body of a person for diagnosis and testing purposes based on images.

The display apparatus 13 is connected to the endoscope processor apparatus 12 and functions as a display unit that displays the motion picture 38 and the still picture 39 input from the endoscope processor apparatus 12. A user (doctor) performs an advancing and receding operation or the like on the insertion part 20 while checking the motion picture 38 displayed on the display apparatus 13. In a case where a lesion or the like is found in the observed part, the user executes imaging of a still picture of the observed part by operating the still picture imaging instruction unit 32 and performs a diagnosis, a biopsy, and the like.

[Medical Image Processing Apparatus]

The medical image processing apparatus 14 classifies the medical image being captured or a region of interest included in the medical image into any of two or more classes mainly based on the time series of medical images, and notifies the user of a classification result. In the present embodiment, for example, a personal computer is used as the medical image processing apparatus 14. In addition, a keyboard, a mouse, and the like connected to the personal computer in a wired or wireless manner are used as the operation unit 15. Various monitors such as a liquid crystal monitor connectable to the personal computer are used as the display (display unit) 16.

<Embodiment of Medical Image Processing Apparatus 14>

Figure 2:
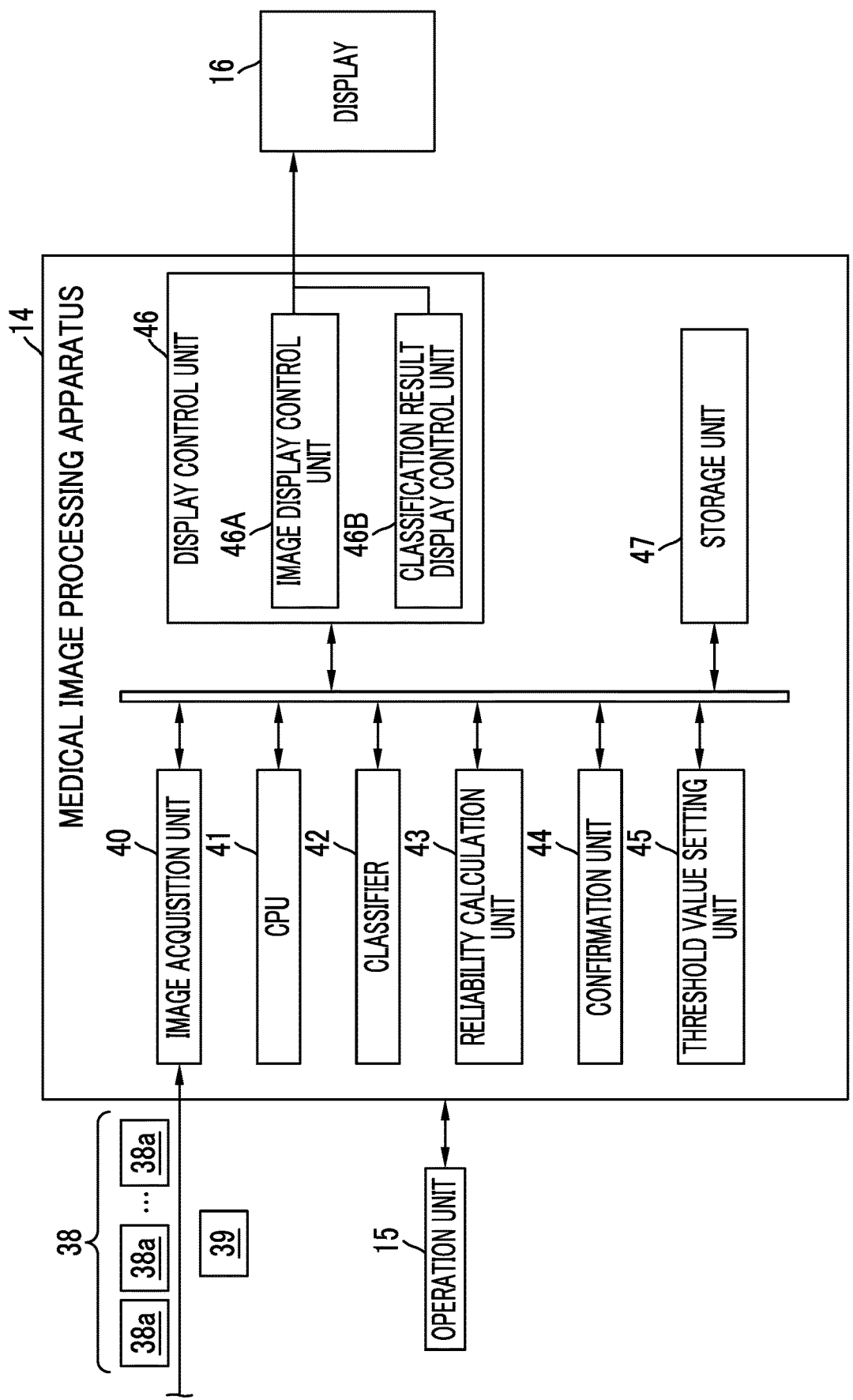
FIG. 2 is a block diagram illustrating an embodiment of a medical image processing apparatus 14.

FIG. 2 is a block diagram illustrating an embodiment of the medical image processing apparatus 14.

The medical image processing apparatus 14 illustrated in FIG. 2 is mainly configured with an image acquisition unit 40, a central processing unit (CPU) 41, a classifier 42, a reliability calculation unit 43, a confirmation unit 44, a threshold value setting unit 45, a display control unit 46, and a storage unit 47.

The CPU 41 operates based on a program stored in the storage unit 47, manages and controls the image acquisition unit 40, the classifier 42, the reliability calculation unit 43, the confirmation unit 44, the threshold value setting unit 45, and the display control unit 46, and functions as a part of each unit thereof.

The image acquisition unit 40 acquires, from the endoscope processor apparatus 12, an image (in the present example, the motion picture 38 imaged by the endoscope 10) consisting of a time series of frame images 38a including the subject image using an image input and output interface, not illustrated, that is connected to the endoscope processor apparatus 12 (FIG. 1) in a wired or wireless manner. In addition, in a case where the still picture 39 is imaged in the middle of imaging of the motion picture 38 in the endoscope 10, the image acquisition unit 40 acquires the motion picture 38 and the still picture 39 from the endoscope processor apparatus 12.

The classifier 42 acquires feature amounts of the frame images 38a based on the time series of frame images 38a acquired by the image acquisition unit 40 and classifies each frame image 38a or the region of interest included in each frame image 38a into any of the two or more classes based on the acquired feature amounts. In the present example, as will be described later, classification is performed into one class of three classes of "neoplastic", "non-neoplastic", and "others" as the two or more classes. However, classes of classification are not limited thereto. For example, classification based on a shape, a size, a position, and the like of a tumor, classification based on severity of a lesion portion, and classification of a combination thereof can be included.

The reliability calculation unit 43 calculates reliability of a classification result of the frame image 38a or the region of interest from the classifier 42. For example, in a case where the classifier 42 calculates a probability of belonging to each class of "neoplastic", "non-neoplastic", and "others", the calculated probability corresponds to the reliability. The reliability of the classification result is not limited to the probability of belonging to each class and can be calculated based on various references.

The confirmation unit 44 confirms the classification result of the frame image 38a or the region of interest based on the reliability of the classification result calculated by the reliability calculation unit 43. Here, confirmation of the classification result is not confirmation of the lesion portion by a confirmed diagnosis based on a pathological diagnosis and refers to confirmation of the classification result based on an automatic diagnosis by the classifier 42.

A method of confirming the classification result can be decided in accordance with a method of calculating the reliability of the classification result. For example, in a case where the reliability of the classification result is quantified, a predetermined numerical value for confirming the classification result can be used as a threshold value, and the classification result can be confirmed in a case where the reliability (numerical value) is greater than or equal to the threshold value. Detailed actions of the reliability calculation unit 43 and the confirmation unit 44 will be described later.

The threshold value setting unit 45 is a part that sets the threshold value necessary for confirming the classification result by the confirmation unit 44. By operating the operation unit 15, the user can use any value as the threshold value to be set by the threshold value setting unit 45. For example, it is considered that the threshold value is increased in a case where the classification result confirmed by the confirmation unit 44 frequently changes, and that the threshold value is decreased in a case where confirmation of the classification result by the confirmation unit 44 requires a long time period.

The display control unit 46 includes an image display control unit 46A that generates display image data based on the medical image (the motion picture 38 and the still picture 39) acquired by the image acquisition unit 40 and outputs the display image data to the display 16, and a classification result display control unit 46B that generates display image data indicating the classification result based on the classification result confirmed by the confirmation unit 44 and outputs the display image data to the display 16.

The display control unit 46 displays the medical image and the classification result on the display 16 by compositing the image data output from the image display control unit 46A with the image data indicating the classification result output from the classification result display control unit 46B and outputting composited image data obtained by compositing to the display 16.

The storage unit 47 includes a storage unit as a work region of the CPU 41 and a storage unit storing various programs such as an operating system and a medical image processing program, the imaged still picture 39, and the like.
<Classifier>

Next, an embodiment of the classifier 42 will be described.

The classifier 42 of the present example includes a convolutional neural network (CNN) for calculating a feature amount from an image (frame image 38a) and performing recognition processing on the image and calculates the feature amount using the color information in the image, a gradient of a pixel value, and the like. The classifier 42 classifies the image or the region of interest included in the image (medical image) into any of a plurality of classes of "neoplastic", "non-neoplastic", and "others" in the present example based on the calculated feature amount.

Figure 3:
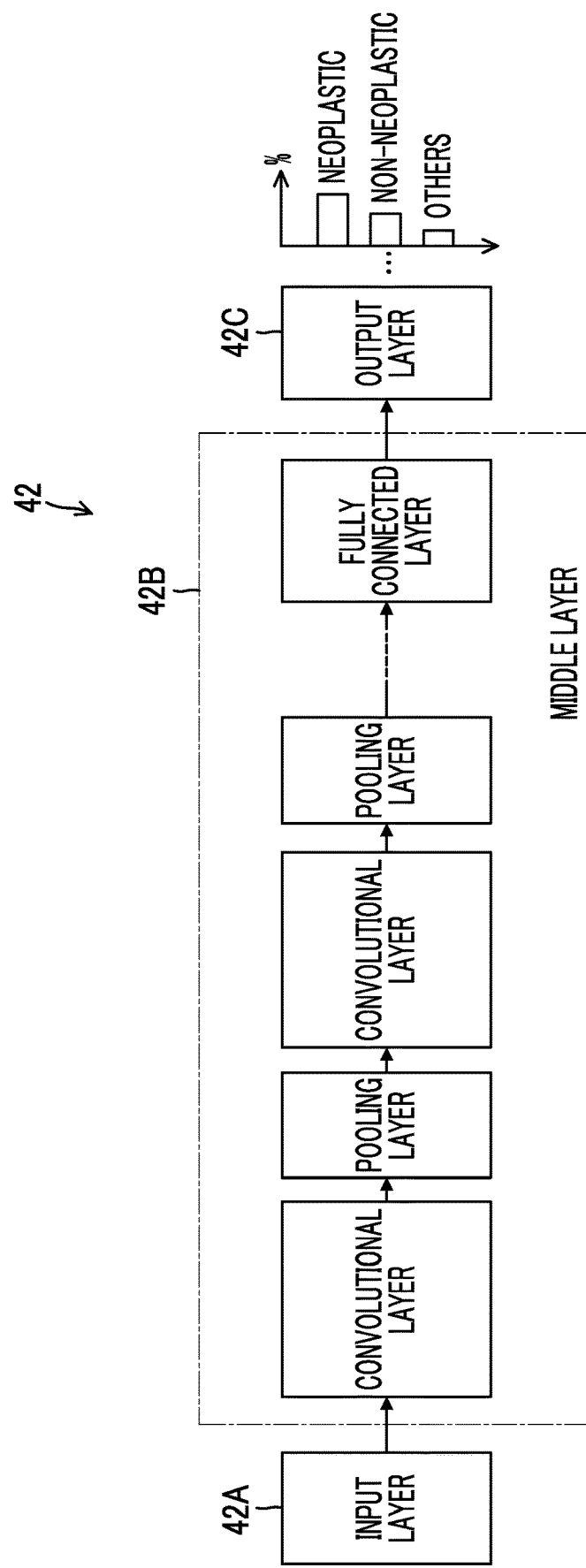
FIG. 3 is a schematic diagram illustrating a representative configuration example of a CNN applied to a classifier 42 of the present example.

FIG. 3 is a schematic diagram illustrating a representative configuration example of the CNN applied to the classifier 42 of the present example.

As illustrated in FIG. 3, the classifier (CNN) 42 comprises an input layer 42A, a middle layer 42B that includes a fully connected layer and a plurality of sets each configured with a convolutional layer and a pooling layer, and an output layer 42C. Each layer has a structure in which a plurality of "nodes" are connected through "edges".

Each frame image 38a of the motion picture 38 is sequentially input into the input layer 42A.

The middle layer 42B includes the fully connected layer and the plurality of sets in which one set is formed with the convolutional layer and the pooling layer, and extracts the feature amount from the frame image 38a input from the input layer. The convolutional layer acquires a "feature map" by performing filter processing (performing convolution calculation using a filter) on a nearby node in the previous layer. The pooling layer forms a new feature map by reducing the feature map output from the convolutional layer. The "convolutional layer" has a role of performing feature extraction such as edge extraction from the image, and the "pooling layer" has a role of providing robustness such that the extracted feature is not affected by translation or the like.

The middle layer 42B is not limited to a case of forming one set with the convolutional layer and the pooling layer. Consecutive convolutional layers may be present, or a normalization layer may be included.

The fully connected layer is a part that is connected in a weighted manner to all nodes of the previous layer and outputs a value (feature variable) converted by an activation function. In the present example, the fully connected layer outputs the feature variable for each classification of the frame image 38a or the region of interest such as the lesion included in the frame image 38a.

The output layer 42C functioning as an inference unit calculates a score (probability) for each classified class by converting an output (feature variable) from the fully connected layer into the probability using a softmax function. In the present example, since the frame image 38a or the region of interest is classified into any of the three classes of "neoplastic", "non-neoplastic", and "others", the output layer 42C outputs a class for which the score is the highest among the scores of the three classes (total of the three scores is 100%), and the score of the class as the classification result.

Parameters of the filter used in each convolutional layer of the middle layer 42B, a weight coefficient of the fully connected layer, and the like are optimized in advance using multiple pieces of learning data.

<First Embodiment of Reliability Calculation Unit 43 and Confirmation Unit 44>

The reliability calculation unit 43 of a first embodiment uses the score (probability) for the classified class included in the classification result of the frame image 38a or the region of interest from the classifier 42 as the reliability. This is because as the score is increased, reliability of the class classified using the score is also increased.

The confirmation unit 44 of the first embodiment confirms the classification result of the frame image 38a or the region of interest from the classifier 42 in a case where the score (reliability) obtained by the reliability calculation unit 43 is greater than or equal to the set threshold value.

For example, in a case where the threshold value is 70%, a class having a score greater than or equal to the threshold value has sufficiently high reliability, compared to other classes (other classes having scores less than or equal to 30%). Accordingly, even in a case where the classification result changes due to a change in score for each class caused by a motion of the living body, a change in imaging position, and the like, it is preferable to confirm and not change the classification result in a case where the classification result having the reliability higher than or equal to the threshold value is obtained.

<Second Embodiment of Reliability Calculation Unit 43 and Confirmation Unit 44>

The confirmation unit 44 of a second embodiment confirms the classification result of the frame image 38a or the region of interest based on a plurality of classification results obtained for the time series of frame images 38a.

Specifically, the reliability calculation unit 43 calculates the number of specific classification results (for example, classification results of "neoplastic") that are the plurality of classification results sequentially calculated for the time series of frame images 38a and have the reliability greater than or equal to the threshold value. In a case of using classification results of 15 consecutive frames, the plurality of classification results are 15 classification results.

The confirmation unit 44 of the second embodiment confirms the specific classification result as the classification result of the frame image 38a or the region of interest in a case where the number of specific classification results having the reliability calculated by the reliability calculation unit 43 greater than or equal to the threshold value is greater than or equal to a reference number. For example, in a case where the reference number for the 15 consecutive frames is 12, the specific classification result is confirmed as the classification result of the frame image 38a or the region of interest in a case where the number of specific classification results is greater than or equal to 12. That is, in a case where 12 frames among the 15 consecutive frames have the specific classification result, the specific classification result is confirmed.

In addition, in a modification example of the confirmation unit 44 of the second embodiment, the specific classification result is confirmed as the classification result of the frame image 38a or the region of interest in a case where a ratio of the number of specific classification results having the reliability calculated by the reliability calculation unit 43 greater than or equal to the threshold value is greater than or equal to a reference ratio. For example, in a case where the reference ratio is 80 percent, the specific classification result is confirmed in a case where the ratio of the number of specific classification results among the plurality of classification results (15 classification results) is greater than or equal to 80 percent.

Accordingly, even in a case where the classification result is not stable due to the motion of the living body, the change in imaging position, and the like, the specific classification result can be confirmed in a case where the number or the ratio of specific classification results is greater than or equal to the reference number or the reference ratio. It is preferable that the number of the plurality of classification results and the reference number or the reference ratio can be set to any value.

<Third Embodiment of Reliability Calculation Unit 43 and Confirmation Unit 44>

The reliability calculation unit 43 of a third embodiment calculates an amount of change in reliability of a specific classification result among the plurality of classification results. For example, in a case where the reliability of the specific classification result is the score (probability) for the classified class, an amount of change (range of change) in score within a set number of frames is calculated. For example, in a case where the set number of frames is five, and the scores of the frames are 50, 60, 55, 65, and 62, the amount of change is 15.

The confirmation unit 44 of the third embodiment confirms the specific classification result as the classification result of the frame image 38a or the region of interest in a case where the amount of change in reliability of the specific classification result is within a reference range. For example, in a case where the reference range is 15, the specific classification result is confirmed because the amount of change in the above case is less than or equal to 15.

It is preferable that the number of frames for calculating the amount of change in reliability of the specific classification result and the reference range for confirming the classification result can be set to any values.

<Another Embodiment of Classifier>

While the classifier 42 of an embodiment illustrated in FIG. 3 classifies the entire medical image or the region of interest in the medical image into any of the plurality of classes, a classifier of another embodiment classifies the medical image into a class for each pixel or region based on the medical image and creates a region image indicating the classification result of the medical image. For example, the classifier of the other embodiment can be configured with a fully convolution network (FCN) not including the fully connected layer.

The region image indicating the classification result of the medical image can be color-coded based on the class of the classification result or have different brightness in accordance with the score included in the classification result, and can be displayed on the display 16.

Figure 4:
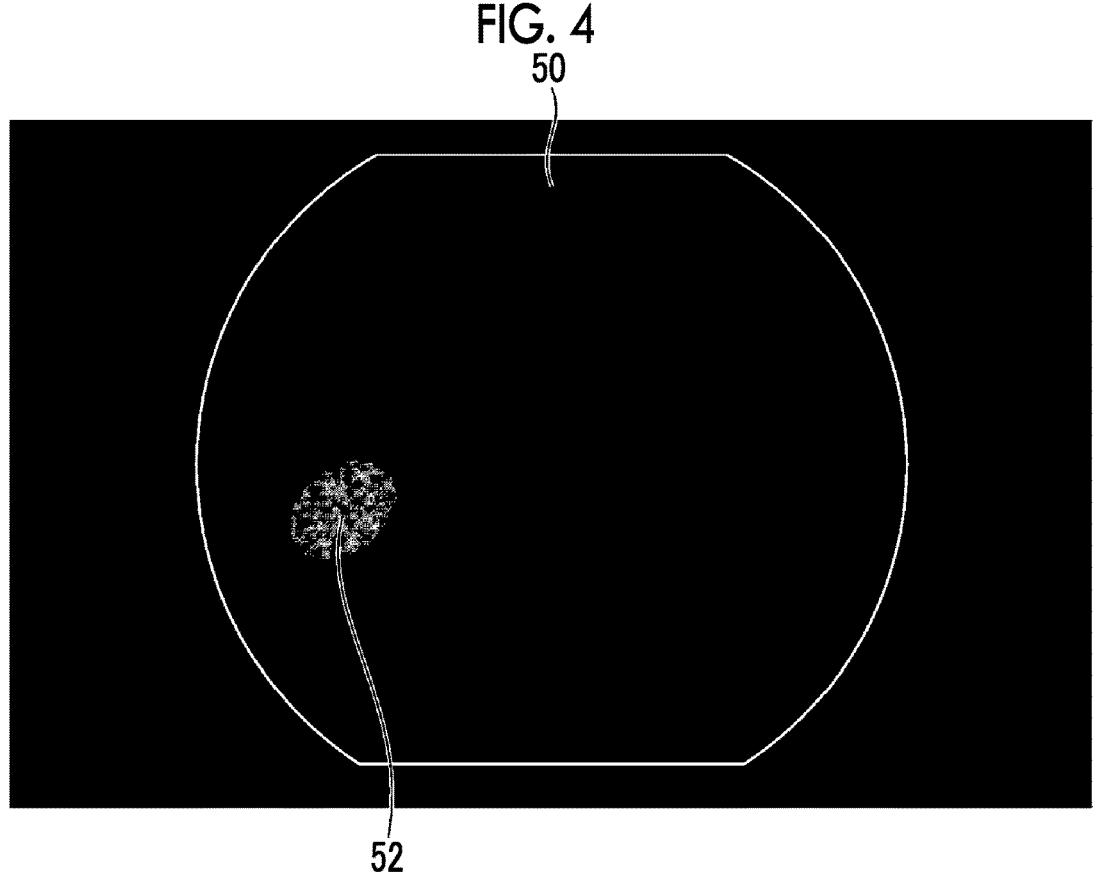
FIG. 4 is a diagram illustrating an example of a region image indicating a classification result of a medical image.

FIG. 4 is a diagram illustrating an example of the region image indicating the classification result of the medical image. The region image displayed on the display 16 is denoted by 50, and the region image corresponding to the region of interest is denoted by 52.

In the following embodiment, the reliability of the classification result of the medical image or the region of interest is calculated using the region image 50 indicating the classification result of the medical image illustrated in FIG. 4.

<Fourth Embodiment of Reliability Calculation Unit 43 and Confirmation Unit 44>

The reliability calculation unit 43 of a fourth embodiment calculates an area of the region of interest 52 in the region image 50 based on the region image 50. A size of the region of interest 52 changes depending on an imaging distance. Thus, it is preferable to calculate the area of the region of interest 52 that is standardized in accordance with the imaging distance.

The confirmation unit 44 of the fourth embodiment confirms the classification result of the medical image or the region of interest 52 in a case where the area of the region of interest 52 calculated by the reliability calculation unit 43 is greater than or equal to a threshold value. As the area occupied by the region of interest 52 in the region image 50 is increased, the confirmation unit 44 increases the reliability of the classification result and confirms the classification result of the region of interest 52.

<Fifth Embodiment of Reliability Calculation Unit 43 and Confirmation Unit 44>

The reliability calculation unit 43 of a fifth embodiment calculates a representative value of the reliability of the classification result for each pixel in the region of interest 52 based on the region image 50. An average value, a center value, a mode value, a maximum value, or the like of the reliability in the region of interest 52 is considered as the representative value.

The confirmation unit 44 of the fifth embodiment confirms the classification result of the medical image or the region of interest 52 in a case where the representative value of the reliability calculated by the reliability calculation unit 43 is greater than or equal to a threshold value.

Here, the reliability of the classification result for each pixel in the region image 50 corresponds to a density for each pixel of the region image 50. As the representative value of the density in the region of interest 52 is increased, the confirmation unit 44 increases the reliability of the classification result and confirms the classification result of the region of interest 52.

<Sixth Embodiment of Reliability Calculation Unit 43 and Confirmation Unit 44>

The reliability calculation unit 43 of a sixth embodiment calculates a variance or a standard deviation of the classification result for each pixel in the region of interest 52 based on the region image 50.

The confirmation unit 44 of the sixth embodiment confirms the classification result of the medical image or the region of interest 52 in a case where the variance or the standard deviation calculated by the reliability calculation unit 43 is less than or equal to a threshold value.

That is, as variations (the variance or the standard deviation) in classification result for each pixel in the region of interest 52 are decreased, the confirmation unit 44 increases the reliability of the classification result for the region of interest 52 and confirms the classification result of the region of interest 52.

<Display Control Unit>

The image display control unit 46A of the display control unit 46 illustrated in FIG. 2 generates the display image data based on the medical image (the motion picture 38 and the still picture 39) acquired by the image acquisition unit 40 and outputs the display image data to the display 16. Accordingly, the display 16 displays the medical image.

In addition, the classification result display control unit 46B generates the display image data indicating the classification result based on the classification result confirmed by the confirmation unit 44 and outputs the display image data to the display 16. Accordingly, the display 16 displays the confirmed classification result of the medical image or the region of interest included in the medical image.

Figure 5:
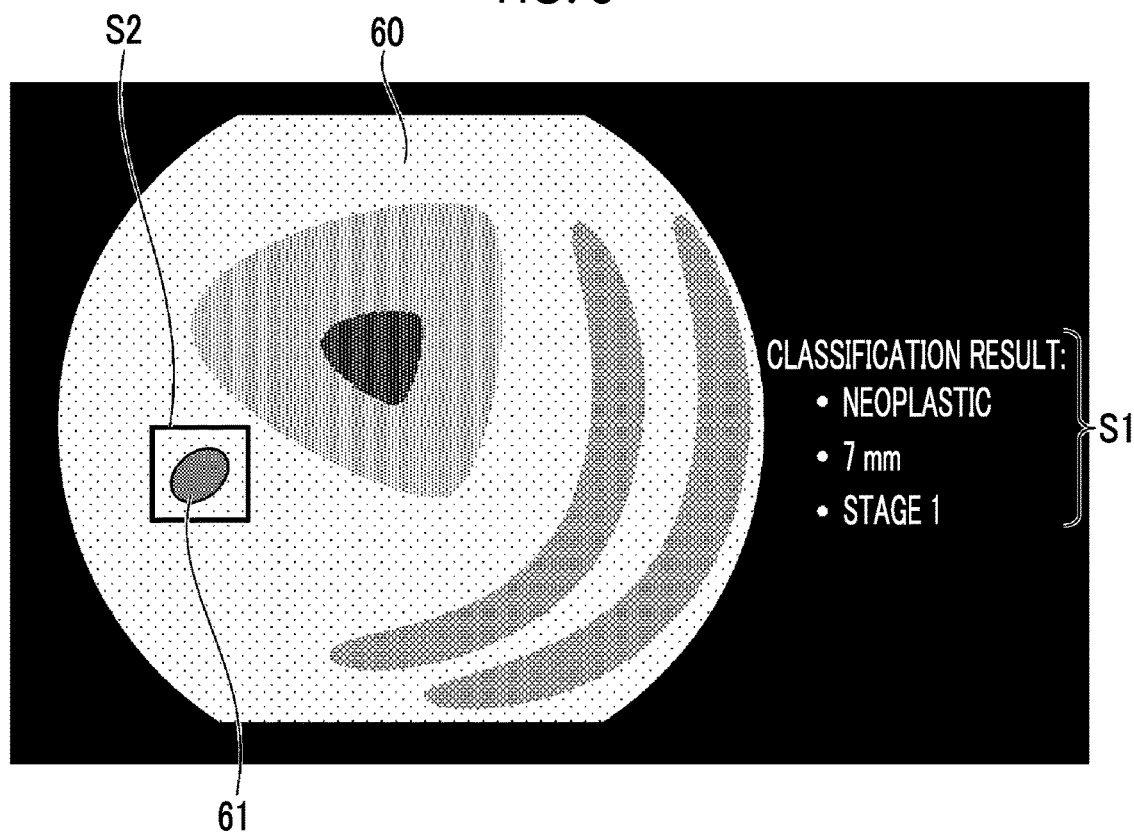
FIG. 5 is a diagram illustrating an example of a medical image 60 and classification results S1 and S2 displayed on a display 16.

FIG. 5 is a diagram illustrating an example of a medical image 60 and classification results S1 and S2 displayed on the display 16.

In FIG. 5, a region of interest included in the medical image 60 is denoted by 61. The classification result S1 of the present example includes a size (in the present example, "7 mm") of the region of interest 61 and the severity (in the present example, a stage classification "stage 1") of the lesion in addition to one class (in the present example, "neoplastic") of the three classes of "neoplastic", "non-neoplastic", and "others".

In addition, the classification result S2 is a figure (rectangular frame) that notifies the user of a position of the region of interest 61. The rectangular frame is created to enclose the region of interest 61 and is displayed in a superimposed manner on the medical image 60. The rectangular frame can be created based on positional information on the region of interest 52 of the region image 50 illustrated in FIG. 4.

The display control unit 46 displays the medical image 60 and the classification results S1 and S2 on the display 16 by compositing the image data output from the image display control unit 46A with the image data indicating the classification result output from the classification result display control unit 46B and outputting composited image data obtained by compositing to the display 16.

In addition, after a composited image of the medical image 60 and the confirmed classification results S1 and S2 is displayed on the display 16, the display control unit 46 can cause the classification results S1 and S2 to be not displayed (display only the medical image 60) after a certain time period (for example, after a few seconds). Only the rectangular frame may be caused to be not displayed. This is not to impede radiological interpretation of the medical image 60.

Furthermore, the classification result display control unit 46B may generate image data indicating the classification result confirmed by the confirmation unit 44 and the classification result (non-confirmed classification result) from the classifier 42 and display the confirmed classification result and the non-confirmed classification result on the display 16. In this case, it is preferable that the confirmed classification result and the non-confirmed classification result are displayed in an identifiable manner using different display forms (for example, color-coding).

[Medical Image Processing Method]

Figure 6:
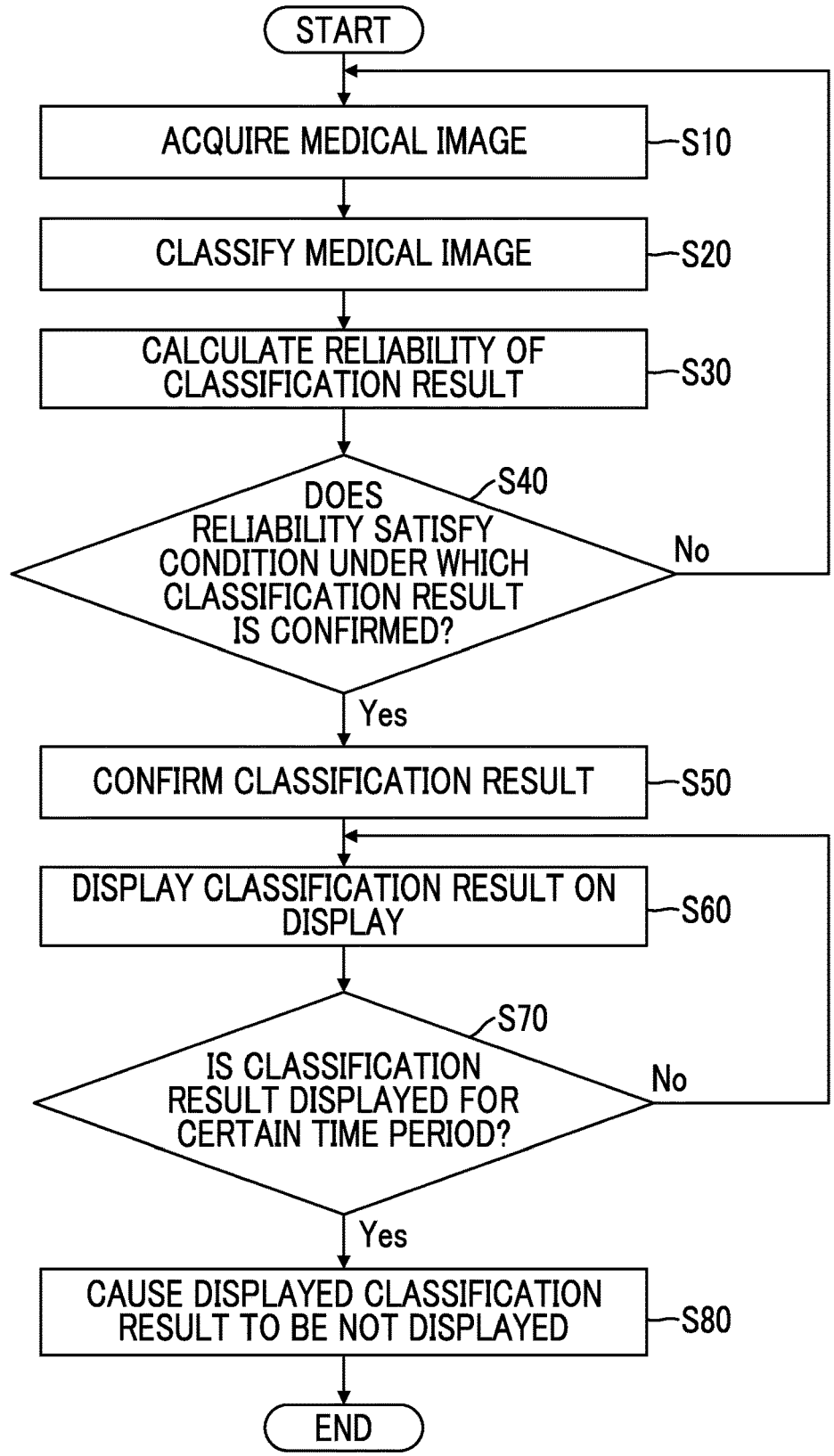
FIG. 6 is a flowchart illustrating an embodiment of a medical image processing method according to the embodiment of the present invention.

FIG. 6 is a flowchart illustrating an embodiment of a medical image processing method according to the embodiment of the present invention, and illustrates a processing procedure of each unit of the medical image processing apparatus 14 illustrated in FIG. 2.

In FIG. 6, the image acquisition unit 40 acquires the medical image of one frame of the time series of medical images of a processing target from the endoscope processor apparatus 12 (step S10).

The classifier 42 obtains the feature amount of the medical image from the medical image acquired in step S10 and classifies the medical image or the region of interest included in the medical image into any of the two or more classes based on the feature amount (step S20).

The reliability calculation unit 43 calculates the reliability of the classification result of the medical image or the region of interest from the classifier 42 (step S30).

The confirmation unit 44 determines whether or not the reliability of the classification result calculated in step S30 satisfies a condition (threshold value) under which the classification result is confirmed (step S40), and confirms the classification result in a case where the condition under which confirmation is made is satisfied (in a case of "Yes") (step S50). In a case where the condition under which confirmation is made is not satisfied (in a case of "No"), a transition is made to step S10, and the medical image of the subsequent frame is acquired in step S10.

The classification result display control unit 46B generates the display image data indicating the confirmed classification result and outputs the generated image data to the display 16. Accordingly, the classification result is displayed on the display 16 (step S60). The time series of medical images are displayed on the display 16, and the classification result is displayed together with the medical image.

The classification result display control unit 46B determines whether or not the classification result is displayed on the display 16 for a certain time period (for example, a few seconds) (step S70). In a case where the classification result is not displayed for the certain time period (in a case of "No"), display of the classification result on the display 16 continues. In a case where the classification result is displayed for the certain time period (in a case of "Yes"), the displayed classification result is caused to be not displayed (step S80).

It is preferable that medical image processing in steps S10 to S80 is repeated in a case where, for example, an observation part of the living body changes or a set time period elapses.

FIG. 7 is a flowchart illustrating an embodiment of processing in steps S20 and S30 of the flowchart illustrated in FIG. 6.

In FIG. 7, the classifier classifies the medical image into the classes for each pixel or region based on the medical image (step S22) and creates the region image 50 (FIG. 4) indicating the classification result of the medical image (step S24).

The reliability calculation unit 43 calculates the area of the region of interest 52 in the region image 50 based on the region image 50 (step S32). The confirmation unit 44 calculates the reliability of the classification result corresponding to the area of the region of interest 52 (step S34). That is, as the area occupied by the region of interest 52 in the region image 50 is increased, the confirmation unit 44 increases the reliability of the classification result.

In step S40 illustrated in FIG. 6, in a case where the reliability corresponding to the area of the region of interest 52 satisfies the condition under which confirmation of the classification result is made (that is, in a case where the area of the region of interest 52 is greater than or equal to the threshold value), the confirmation unit 44 confirms the classification result of the region of interest 52.

OTHERS

The classifier according to the embodiment of the present invention is not limited to a classifier that classifies the medical image or the region of interest included in the medical image using a learner such as a CNN, and may be a classifier that detects the region of interest by analyzing a feature amount such as color in the medical image, the gradient of the pixel value, a shape, and a size by image processing, and classify the medical image or the region of interest included in the medical image into any of the two or more classes using the feature amount of the detected region of interest. Alternatively, this classifier may be used together with the learner.

In addition, instead of disposing the image display control unit 46A, the medical image processing apparatus 14 may display the classification result generated by the classification result display control unit 46B in a superimposed manner on the image (the motion picture or the still picture) displayed by the endoscope processor apparatus 12.

While the endoscope processor apparatus 12 and the medical image processing apparatus 14 are separately disposed in the embodiment, the endoscope processor apparatus 12 and the medical image processing apparatus 14 may be integrated. That is, the endoscope processor apparatus 12 may be provided with a function as the medical image processing apparatus 14.

Furthermore, a hardware structure for executing various controls of the medical image processing apparatus 14 of the embodiment includes various processors illustrated as follows. The various processors include a central processing unit (CPU) that is a general-purpose processor functioning as various control units by executing software (program), a programmable logic device (PLD) such as a field programmable gate array (FPGA) that is a processor having a circuit configuration changeable after manufacturing, and a dedicated electric circuit or the like such as an application specific integrated circuit (ASIC) that is a processor having a circuit configuration dedicatedly designed to execute a specific type of processing.

One processing unit may be configured with one of the various processors or may be configured with a combination of two or more processors of the same type or different types (for example, a plurality of FPGAs or a combination of the CPU and the FPGA). In addition, a plurality of control units may be configured with one processor. As an example of configuring the plurality of control units with one processor, first, as represented by a computer such as a client or a server, a form of configuring one processor with a combination of one or more CPUs and software and causing the processor to function as the plurality of control units is present. Second, as represented by a system on chip (SoC) or the like, a form of using a processor that implements the function of the entire system including the plurality of control units using one integrated circuit (IC) chip is present. Accordingly, various control units are configured using one or more of the various processors as the hardware structure.

In addition, while the time series of images or the still picture imaged by the endoscope 10 is used as the medical image of the processing target in the embodiment, the present invention is not limited thereto. For example, a medical image captured by other modalities such as an ultrasound diagnostic apparatus and an X-ray imaging apparatus may be used.

Furthermore, the present invention is not limited to the embodiment and can be subjected to various modifications without departing from a spirit of the present invention.

EXPLANATION OF REFERENCES

9: endoscope system
10: endoscope
11: light source apparatus
12: endoscope processor apparatus
13: display apparatus
14: medical image processing apparatus
15: operation unit
16: display
20: insertion part
21: hand operation unit
22: universal cord
25: flexible portion
26: bending portion
27: distal end portion
28: imaging element
29: bending operation knob
30: air supply and water supply button
31: suction button
32: still picture imaging instruction unit
33: treatment tool introduction port
35: light guide
36: signal cable
37a: connector
37b: connector
38: motion picture
38a: frame image
39: still picture
40: image acquisition unit
41: CPU
42: classifier
42A: input layer
42B: middle layer 42C: output layer
43: reliability calculation unit
44: confirmation unit
45: threshold value setting unit
46: display control unit
46A: image display control unit
46B: classification result display control unit
47: storage unit
50: region image
52, 61: region of interest
60: medical image
S1, S2: classification result
S10 to S80: step

What is claimed is:

1. An endoscope system comprising:
a light source apparatus configured to generate illumination light for a subject;
an endoscope including an imaging element configured to image the subject irradiated with the illumination light; and
a medical image processing apparatus configured to acquire a medical image obtained by imaging the subject by the imaging element, wherein the medical image processing apparatus is configured to acquire the medical image by irradiating the subject with the illumination light having a peak wavelength in a wavelength range of greater than or equal to 390 nm and less than or equal to 450 nm from the light source apparatus via the endoscope,
the medical image processing apparatus comprising one or more processors configured to:
acquire the medical image;
output a region of interest included in the medical image and classification information on the region of interest, the region of interest and the classification information having been obtained from a classifier by inputting the medical image to the classifier; and
confirm the classification information on the region of interest according to an area of the region of interest,
wherein the medical image or region of interest included in the medical image is classified into any of two or more classes for each pixel or region based on the medical image.

2. The endoscope system according to claim 1, wherein the one or more processors are configured to confirm the classification information on the region of interest in a case where the area of the region of interest is greater than or equal to a threshold value.

3. The endoscope system according to claim 2, wherein the one or more processors are configured to display a classification result of the region of interest, a size of the region of interest or a severity of the region of interest by characters on a monitor.

4. The endoscope system according to claim 3, wherein the one or more processors are configured to display a figure indicating a position of the region of interest in a superimposed manner on the medical image.

5. The endoscope system according to claim 1, wherein the region of interest includes a lesion.

6. The endoscope system according to claim 1, wherein the classification information includes information on a class from among two or more classes, and
the two or more classes include a class of neoplastic and a class of non-neoplastic.

7. The endoscope system according to claim 2, wherein the one or more processors are configured to set the threshold value to any value by an operation of a user.

8. An endoscope system comprising:
a light source apparatus configured to generate illumination light for a subject;
an endoscope including an imaging element configured to image the subject irradiated with the illumination light; and
a medical image processing apparatus configured to acquire a medical image obtained by imaging the subject by the imaging element, wherein the medical image processing apparatus is configured to acquire the medical image by irradiating the subject with the illumination light having a peak wavelength in a wavelength range of greater than or equal to 390 nm and less than or equal to 450 nm from the light source apparatus via the endoscope,
the medical image processing apparatus comprising one or more processors configured to:
obtain an area of a region of interest and classification information on the region of interest, the area and the classification information having been obtained from the region of interest included in the medical image; and
display the classification information on the region of interest on a monitor in a case where the area of the region of interest is greater than or equal to a threshold value,
wherein the medical image or region of interest included in the medical image is classified into any of two or more classes for each pixel or region based on the medical image.

9. The endoscope system according to claim 8, wherein the one or more processors are configured to:
obtain positional information on the region of interest; and
display a region image corresponding to the region of interest based on the positional information on the monitor.

10. The endoscope system according to claim 9, wherein the one or more processors are configured to display the region image corresponding to the region of interest on the monitor by color-coding the region image based on the classification information on the region of interest.

11. The endoscope system according to claim 8, wherein the one or more processors are configured to display the classification information on the region of interest by characters on the monitor.

12. The endoscope system according to claim 11, wherein the classification information includes a classification result of the region of interest, a size of the region of interest or a severity of the region of interest.

13. The endoscope system according to claim 9, wherein the one or more processors are configured to display, on the monitor, the region of interest in a case where the area of the region of interest is greater than or equal to the threshold value and the region of interest in a case where the area of the region of interest is less than the threshold value, using display forms different from each other.

14. The endoscope system according to claim 8, wherein the one or more processors are configured to:
display the medical image on the monitor; and
display a figure that notifies a user of a position of the region of interest in a superimposed manner on the medical image in a case where the area of the region of interest is greater than or equal to the threshold value.

15. The endoscope system according to claim 14, wherein the figure includes a rectangular frame surrounding the region of interest.

16. The endoscope system according to claim 8, wherein the region of interest includes a lesion.

17. The endoscope system according to claim 8, wherein the one or more processors are configured to classify the region of interest into a class from among two or more classes.

18. The endoscope system according to claim 17, wherein the two or more classes include a class of neoplastic and a class of non-neoplastic.

19. The endoscope system according to claim 8, wherein the one or more processors are configured to display the classification information on the region of interest on the monitor for a certain time period, and then cause the displayed classification information to be not displayed.

20. An endoscope system comprising:
a light source apparatus configured to generate illumination light for a subject;
an endoscope including an imaging element configured to image the subject irradiated with the illumination light; and
a medical image processing apparatus configured to acquire a medical image obtained by imaging the subject by the imaging element, wherein the medical image processing apparatus is configured to acquire the medical image by irradiating the subject with the illumination light having a peak wavelength in a wavelength range of greater than or equal to 390 nm and less than or equal to 450 nm from the light source apparatus via the endoscope,
the medical image processing apparatus comprising
one or more processors configured to:
acquire positional information on a region of interest;
display a region image corresponding to the region of interest based on the positional information on a monitor;
acquire an area of the region of interest and a classification information on the region of interest obtained from the region of interest included in the medical image; and
display the classification information on the region of interest, the area of which is greater than or equal to a threshold value, on the monitor.

21. The endoscope system according to claim 20, wherein the medical image or the region of interest included in the medical image is classified into one of two or more classes for each pixel or region based on the medical image.

22. The endoscope system according to claim 21, wherein the one or more processors are configured to display a classification information on the region of interest by characters on the monitor.

23. The endoscope system according to claim 22, wherein the one or more processors are configured to display the region image corresponding to the region of interest on the monitor by color-coding the region image based on the classification information on the region of interest.

24. The endoscope system according to claim 23, wherein the one or more processors are configured to display a figure indicating a position of the region of interest in a superimposed manner on the medical image.

* * * * *